United States Patent [19]

Earnest

[11] 4,401,605
[45] Aug. 30, 1983

[54] PROCESS FOR SCAVENGING SULFUR MONOCHLORIDE FROM THE REACTION MIXTURE FROM THE CHLORINATION OF DIALKYLDITHIOPHOSPHORIC ACID TO DIALKYLTHIOPHOSPHORIC ACID CHLORIDE

[75] Inventor: Steven E. Earnest, Gladstone, Mo.

[73] Assignee: Mobay Chemical Corporation, Kansas City, Mo.

[21] Appl. No.: 377,880

[22] Filed: May 13, 1982

[51] Int. Cl.³ .............................................. C07F 9/20
[52] U.S. Cl. ..................................... 260/990; 260/960
[58] Field of Search ................................ 260/990, 960

[56] References Cited

U.S. PATENT DOCUMENTS 3,089,890  5/1963  Chupp ................................. 260/990
3,897,523  7/1975  Sorstokke .......................... 260/986

FOREIGN PATENT DOCUMENTS 1801432  9/1972  Fed. Rep. of Germany.
2538310  3/1977  Fed. Rep. of Germany.

Primary Examiner—Anton H. Sutto
Attorney, Agent, or Firm—Sprung, Horn, Kramer & Woods

[57] ABSTRACT

There is contemplated in the production of an O,O-dialkyl-phosphorothioic acid chloride of the formula

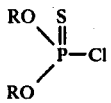

in which R is alkyl, wherein a chlorinating agent is reacted with a bis(thiophosphono) sulfide of the formula

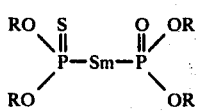

in which m is a whole number, or with a dithiophosphoro compound of the formula

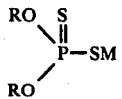

in which M is hydrogen or an alkali metal, to produce a mixture comprising the desired acid chloride, some unreacted starting material and by-products including sulfur monochloride, and the desired acid chloride is separated from the balance of the mixture, the improvement which comprises contacting the mixture before separation with phosphorus trichloride, thereby to convert some of the unreacted starting material to additional desired acid chloride and to convert some of the sulfur monochloride to thiophosphoryl chloride, and distilling off the thiophosphoryl chloride, thereby avoiding precipitation of solid sulfur as occurs upon standing of sulfur monochloride.

3 Claims, No Drawings

PROCESS FOR SCAVENGING SULFUR MONOCHLORIDE FROM THE REACTION MIXTURE FROM THE CHLORINATION OF DIALKYLDITHIOPHOSPHORIC ACID TO DIALKYLTHIOPHOSPHORIC ACID CHLORIDE

The present invention relates to an improvement in the processing of the reaction mixture obtained in the chlorination of O,O-dialkyl-phosphorodithioic acids and derivatives.

It is known to produce various insecticidally active O,O-dialkyl-S-aryl-dithiophosphoric acid esters by reacting O,O-dialkyl-thiophosphoric acid chloride with alkali metal phenolates, e.g. with sodium p-nitro-phenate to produce the known insecticide O,O-diethyl-S-p-nitrophenyl-dithiophosphoric acid ester.

The O,O-dialkyl-thiophosphoric acid chloride starting materials are produced in large quantity by chlorinating O,O-dialkyl-dithiophosphoric acid esters, salts thereof and derivatives thereof such as bis-sulfides. As described in U.S. Pat. No. 3,089,890, the diester chlorides are obtained commercially by a variety of processes, e.g., by chlorinating (preferably in an anhydrous system and either in the presence or absence of inert organic solvent) either (1) a bis(thiophosphono) sulfide of the structure

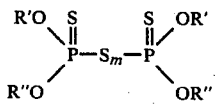

wherein m is a whole number, but usually 2, or (2) a dithiophosphoro compound (which may be the precursor of (1)) of the structure

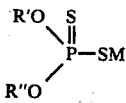

wherein M is hydrogen or an alkali metal (e.g. sodium or potassium) but usually hydrogen, the chlorinating agent being chlorine or sulfur dichloride or sulfur monochloride or sulfuryl chloride but usually chlorine. Illustrative of the various commercial processes employed are the following wherein M is hydrogen or an alkali metal and wherein X is the grouping

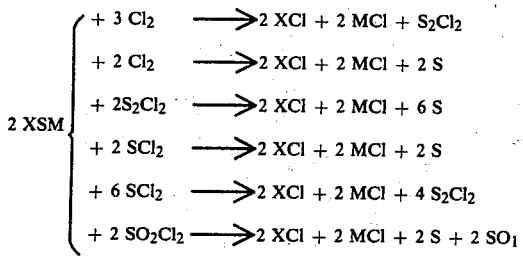

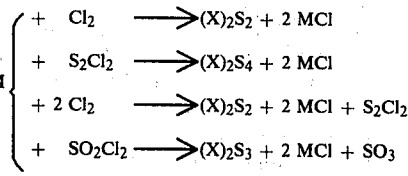

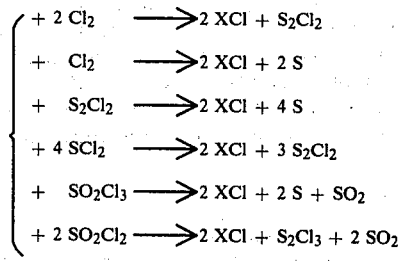

However, these reactions are not so simple as set forth above in that a variety of side reaction products are formed to varying extents depending upon the reaction conditions and the reactants, e.g. the type and amount of chlorinating agent as well as the purity of the thiophosphoro compound subjected to chlorination.

U.S. Pat. No. 3,897,523 refers to U.S. Pat. No. 3,089,890 and discloses a way of carrying out the reaction to obtain a mixture of products necessitating thin film evaporation to separate the desired product.

German Laid Open Specification DOS No. 2,538,310 also relates to a similar process, resulting in precipitated sulfur and refers to a still earlier process shown in German Pat. No. 1,801,432.

The sulfur monochloride by-product which is produced in various of the processes, upon standing in the reaction mixture decomposes to liberate solid sulfur. This sulfur entrains the mixture, agglomerates to form soft lumps which clog the system, interfering with the distillation of the desired ester chloride.

It is accordingly an object of the present invention to eliminate sulfur monochloride from a chlorination product of the nature described, and thereby avoid precipitation of solid sulfur.

This and other objects and advantages are realized in accordance with the present invention pursuant to which the crude chlorination product mixture of the character described is contacted with phosphorus trichloride. Thereby sulfur which is present or which forms is converted to thiophosphoryl chloride and unreacted starting material is converted to additional desired product, i.e., the initial chlorination is carried forward to a greater degree. Thereafter the thiophosphoryl chloride and O,O-dialkyl-thiophosphoric acid ester chloride are separated from one another and from any other components of the reaction mass, advantageously by distillation.

The initial chlorination can be effected in known manner with any of the hereinbefore noted chlorinating agents, e.g. sulfur chlorides or sulfuryl chloride or preferably chorine per se. Advantageously the chlorinating agent is used in approximately stoichiometric amount although an excess may be used to drive the reaction to completion, all in known manner.

The alkyl radicals of the starting O,O-dialkyldithiophosphoric acid or derivative thereof advantageously have from 1 to 4 carbon atoms O,O-dimethyl- and O,O-diethyl- being preferred.

To the chlorination mass the phosphorus trichloride is added. The time and temperature of reaction can vary widely, but to ensure complete reaction at least about 30 minutes at about room temperature and preferably at least about 1 hour at about 50° C. is desirable after the addition of phosphorus trichloride is complete. The phosphorus trichloride is advantageously added in at least stoichiometric amount based on the sulfur monochloride content, in accordance with the equation:

$$2PCl_3 + S_2Cl_2 \rightarrow 2PSCl_3 + Cl_2.$$

Thus, in addition to scavenging the sulfur monochloride the phosphorus trichloride effectively generates additional chlorine to complete chlorination of any unreacted starting material present in the product. The sulfur monochloride content can be determined by assay in conventional manner. It may run from about 2 to 17 and advantageously about 2 to 4% by weight of the chlorination reaction mass, exclusive of any solvent which might have been employed (although preferably no such solvent is employed). Advantageously the phosphorus trichloride is employed in about 2 to 10% excess.

The scavenged product is then distilled to recover the desired product and thiophosphoryl chloride, any distillation residue of unreacted phosphorus trichloride, thiophosphoryl chloride and diester chloride being carried over for the next cycle.

The invention will be further described in the following illustrative examples wherein all parts are by weight unless otherwise expressed.

EXAMPLE 1

(a) To 200 g of a crude chlorination mixture containing O,O-dimethyl-thiophosphoric acid chloride and 4% by weight of sulfur monochloride, produced as described in Example IV of U.S. Pat. No. 3,089,890 or U.S. Pat. No. 3,897,523, at 10° C. there are added 142.5 g of phosphorus trichloride and the mass is stirred for 10 minutes at 10° C. The mixture is then heated to 50° C. for a cook period of 60 minutes. Once the cook is finished, the mixture is crudely distilled to a vacuum of 3–5 mm Hg and a maximum pot temperature of 75° C., leaving a distillation residue which is recycled to the next batch. The average distillate is 325.5 g with a composition of 47% PSCl$_3$ and 46% O,O-dimethylthiophosphoryl chloride.

(b) 651 g of crude distillate from (a) is charged to a 1 liter flask equipped with a fractionating column containing a 9"×1.25" packed (6 mm Berl saddles) section. At a pressure of 8–10 mm Hg and a reflux ratio of 1:1, the PSCl$_3$ is removed. The pot temperature reaches 62° C., with an overhead of 24° C. When the PSCl$_3$ has been removed, the O,O-dimethylthiophosphoryl chloride can be isolated either by (i) continuation of the distillation or
(ii) by removing the vacuum, washing the bottoms in the normal manner, then followed by separation and redistillation to give the final product. Typical yields for the latter process is 269 g of PSCl$_3$, containing about 3.2% of diester chloride and 291 g of O,O-dimethylthiophosphoryl chloride (98.0% purity).

This represents a yield of 88.1% assuming 100% purity for the initial O,O-dimethyldithiophosphoric acid ester.

EXAMPLE 2

(a) 219.5 g of a chlorination product containing O,O-diethyl-thiophosphoric acid diester chloride and 4% by weight of sulfur monochloride (as in Example 1-a) are combined with 150 g of phosphorus trichloride and stirred at 10° C. for 10 minutes. The mixture is then heated to 50° C. for a 60-minute cook period, followed by a crude distillation at 3–5 mm Hg. and a maximum pot temperature of 90° C. As in Example 1-b, the heels from the crude distillation are recycled to subsequent batches. The average crude distillate is 343.5 g containing 36.2 PSCl$_3$ and 52.6% O,O-diethylthiophosphoryl chloride.

(b) Using the same apparatus and conditions as found in Example 1-b, the PSCl$_3$ is removed and the O,O-diethylthiophosphoryl chloride purified. Typical yield is 261.2 g of PSCl$_3$ containing 1% of the diester chloride and 348.1 g (98.5% purity) of O,O-diethylphosphoryl chloride. This gives an in-hand yield of 90.9% based on 100% pure starting material.

It will be understood that the specification and examples are illustrative but not limitative of the present invention and that other embodiments within the spirit and scope of the invention will suggest themselves to those skilled in the art.

What is claimed is:

1. In the production of an O,O-dialkylphosphorothioic acid chloride of the formula

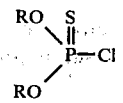

in which R is alkyl, wherein a chlorinating agent is reacted with a bis(thiophosphono) sulfide of the formula

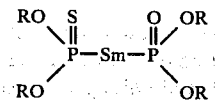

in which m is a whole number, or with a dithiophosphoro compound of the formula

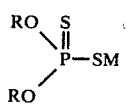

in which M is hydrogen or an alkali metal to produce a mixture comprising the desired acid chloride, some unreacted starting material and by-products including sulfur monochloride; and the desired acid chloride is separated from the balance of the mixture, the improvement which comprises contacting the mixture before separation with phosphorus trichloride, thereby to convert some of the unreacted starting material to additional desired acid chloride and to convert some of the sulfur monochloride to thiophosphoryl chloride, and distilling off the thiophosphoryl chloride, thereby avoiding precipitation of solid sulfur as occurs upon standing of sulfur monochloride.

2. The process according to claim 1, wherein the phosphorus trichloride is employed in at least about twice the molar amount of the sulfur monochloride calculated as $S_2Cl_2$.

3. The process according to claim 2, wherein R is methyl or ethyl, the starting material is an O,O-dialkyl-dithiophosphoric acid diester and the chlorinating agent is chlorine.

* * * * *